United States Patent
Rademacher et al.

(10) Patent No.: US 8,906,406 B2
(45) Date of Patent: Dec. 9, 2014

(54) MUCOADHESIVE DISPERSIBLE PHARMACEUTICAL PREPARATION FOR ACTIVE-AGENT DOSING IN VETERINARY AND HUMAN MEDICINE

(75) Inventors: Tina Rademacher, Bad Breisig (DE); Frank Seibertz, Rheinbrohl (DE); Petra Brandt, Rengsdorf (DE); Markus Krumme, Neuwied (DE); Christian Von Falkenhausen, Meckenheim (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1837 days.

(21) Appl. No.: 10/468,230

(22) PCT Filed: Feb. 8, 2002

(86) PCT No.: PCT/EP02/01314
§ 371 (c)(1),
(2), (4) Date: Nov. 14, 2003

(87) PCT Pub. No.: WO02/066016
PCT Pub. Date: Aug. 29, 2002

(65) Prior Publication Data
US 2004/0081699 A1 Apr. 29, 2004

(30) Foreign Application Priority Data
Feb. 19, 2001 (DE) .................. 101 07 659

(51) Int. Cl.
| A61K 9/00 | (2006.01) |
| A61K 9/28 | (2006.01) |
| A61F 2/00 | (2006.01) |
| A61F 13/00 | (2006.01) |
| A61K 47/00 | (2006.01) |
| A61K 9/20 | (2006.01) |
| A61K 9/70 | (2006.01) |

(52) U.S. Cl.
CPC .............. *A61K 9/0056* (2013.01); *A61K 9/2072* (2013.01); *A61K 9/006* (2013.01); *A61K 9/7007* (2013.01)
USPC ........... 424/441; 424/400; 424/428; 424/434; 424/435; 424/439

(58) Field of Classification Search
None
See application file for complete search history.

(56) References Cited

U.S. PATENT DOCUMENTS

| 3,972,995 A | 8/1976 | Tsuk et al. |
| 4,175,326 A | 11/1979 | Goodson |
| 4,250,163 A * | 2/1981 | Nagai et al. ................ 514/772.1 |
| 4,329,333 A | 5/1982 | Barr |
| 4,597,959 A | 7/1986 | Barr |
| 4,777,033 A | 10/1988 | Ikura et al. |
| 4,948,580 A | 8/1990 | Browning |
| 5,225,196 A | 7/1993 | Robinson |
| 5,318,779 A | 6/1994 | Hakamatsuka et al. |
| 5,472,704 A * | 12/1995 | Santus et al. .................. 424/435 |
| 5,516,522 A | 5/1996 | Peyman et al. |
| 5,643,582 A * | 7/1997 | Gangadharan et al. ....... 424/401 |
| 5,648,093 A * | 7/1997 | Gole et al. ..................... 424/484 |
| 5,750,136 A | 5/1998 | Scholz et al. |
| 5,800,832 A * | 9/1998 | Tapolsky et al. .............. 424/449 |
| 5,807,576 A | 9/1998 | Allen, Jr. et al. |
| 5,908,637 A | 6/1999 | Benes et al. |
| 5,942,243 A | 8/1999 | Shah |
| 6,027,748 A * | 2/2000 | Conte et al. .................... 424/458 |
| 6,066,337 A | 5/2000 | Allen et al. |
| 6,180,682 B1 | 1/2001 | Place |
| 6,231,957 B1 * | 5/2001 | Zerbe et al. .................... 428/220 |
| 6,497,899 B2 * | 12/2002 | Thombre et al. .............. 424/464 |
| 6,531,151 B1 * | 3/2003 | Besse ............................. 424/464 |
| 6,552,024 B1 * | 4/2003 | Chen et al. ................ 514/252.16 |
| 6,635,281 B2 | 10/2003 | Wong et al. |
| 2003/0129219 A1 * | 7/2003 | Hong et al. .................... 424/449 |

FOREIGN PATENT DOCUMENTS

| DE | 196 46 392 A | 5/1998 |
| DE | 196 52 257 A | 6/1998 |
| EP | 0710491 | 5/1996 |
| WO | WO 95/33452 | 12/1995 |
| WO | WO 99/17868 | 4/1999 |
| WO | WO 00/18365 A | 4/2000 |
| WO | WO 00/35418 A | 6/2000 |
| WO | WO 01/34121 A | 5/2001 |
| WO | WO 01/39836 | 6/2001 |
| WO | WO 02/02085 A | 1/2002 |

OTHER PUBLICATIONS

ShinEtsu, Methylcellulose USP, Hypromellose USP, Metolose, downloaded online Nov. 26, 2013.*

* cited by examiner

*Primary Examiner* — Michael G Hartley
*Assistant Examiner* — Nabila Ebrahim
(74) *Attorney, Agent, or Firm* — ProPat, L.L.C.

(57) ABSTRACT

The invention relates to a mucoadhesive medicinal preparation for administering active substances in veterinary or humane medicine, containing at least one active substance, which preparation is characterized in that it is a mucoadhesive matrix disintegratable in aqueous media, which matrix contains at least one matrix-forming polymer and wherein at least one active substance is dissolved or dispersed, and in that the said preparation disintegrates or erodes within maximally 15 minutes after introduction in an aqueous medium or in body fluids, or in that the preparation initially gels within maximally 15 min after its introduction in an aqueous medium or in body fluids, and disintegrates or erodes within maximally 30 min after said introduction.

20 Claims, No Drawings

MUCOADHESIVE DISPERSIBLE PHARMACEUTICAL PREPARATION FOR ACTIVE-AGENT DOSING IN VETERINARY AND HUMAN MEDICINE

This application is the national phase under 35 U.S.C. §371 of PCT International Application No. PCT/EP02/01314 which has an International filing date of Feb. 8, 2002, which designated the United States of America.

The invention relates to mucoadhesive medicinal preparations which quickly disintegrate in aqueous media, for administration of medicinal active substances in cavities of the animal and human body which are lined with mucosa.

Oral administration of active substances in veterinary medicine frequently involves special problems and effort since the animal to be treated often refuses to take the medicament. Thus in the case of domestic cats, for example, a drug therapy by way of oral active substance application involves extreme effort and is extremely difficult since the cats strongly resist taking drops or tablets. Even if the medicament to be administered is mixed, for example in the form of solid particles, with the animal feed, this is mostly unsuccessful since the animals, when feeding, selectively avoid to take in the medicament particles and only ingest the medicament-free food. If oral intake does nevertheless occur, the medicament is mostly spit out immediately, since the animal perceives the medicament as a foreign body or assumes it to be poisonous or not fit to eat. The keeper of the animal must therefore apply the administration form directly, that is, introduce the same deeply into the animal's throat and possibly prevent the animal from spitting it out by holding its mouth closed. In particular, as is well-known, the handling of cats in this way involves extremely great effort and usually necessitates wearing protective gloves. For this reason, many pet or livestock owners prefer medication by the veterinary, which entails additional costs. Furthermore, the mode of administration described puts the animal which is being treated under relatively great stress. In addition, because of the circumstances mentioned, it is difficult to make sure that the animal actually takes up the prescribed dose of active ingredient.

It was therefore the task of the present invention to provide administration forms by means of which the above-mentioned problems involved in the administration of medicaments to animals, especially in oral administration, are avoided or at least reduced.

According to the invention this task is solved by mucoadhesive medicinal preparations according to claims 1 and 2, and by the preferred embodiments described in the subclaims.

The medicinal preparations stand out for having a mucoadhesive matrix disintegratable in aqueous media, which matrix is formed of at least one matrix-forming polymer and has at least one active substance dissolved or dispersed therein; optionally, this matrix may also contain one or more auxiliary substances. An essential feature of the medicinal preparations according to the invention is furthermore the fact that they quickly disintegrate after having been inserted into an aqueous medium or in body fluids, i.e. within maximally 15 min after insertion.

According to a further embodiment of the invention it is provided for the preparation to gel within a maximum of 15 min after having been introduced in an aqueous medium or in body fluids, and to disintegrate or erode within a maximum of 30 min following this introduction.

Mucoadhesive administration forms have already been described several times, these administration forms are, however, not quickly disintegrating. U.S. Pat. No. 5,750,136 describes a mucoadhesive administration form adhering to the mucosa and enabling a persistent, retarded active substance delivery. Furthermore, in U.S. Pat. No. 5,908,637 there is described a mucoadhesive administration form which is suitable for delivering heparine and enables prolonged delivery of the active substance to the mucous membrane. In U.S. Pat. No. 5,942,243 there is disclosed a mucoadhesive administration form for delivery of active substance to animals which causes a continuous, retarded delivery of active substance. Further reference is made to U.S. Pat. No. 4,948,580, wherein a bioadhesive formula is described which can be used as an oral release medium for steroid, antibacterial and fungicidal active substances and can be produced from a freeze-dried polymer mixture. Finally, from U.S. Pat. No. 5,225,196 there is known a bioadhesive formula for controlled active substance delivery which contains a polymer swellable in water which is, however, crosslinked and water-insoluble. None of the mentioned mucoadhesive medicament forms has the property of quickly disintegrating in aqueous media (i.e. within 15 min).

The essential advantage of the medicinal preparations of the invention consists in that the mucoadhesive, rapidly disintegrating medicament form only needs to come into contact with the target mucosa of the animal being treated for a short time to cause the medicament form to adhere strongly to the surface of the mucosa. As a result, the medicament can no longer be spit out or shaken off by the animal. This is achieved mainly by means of the mucoadhesive formulation of the medicinal preparation. As soon as the medicinal preparation absorbs moisture, as is to be expected when coming into contact with mucosae, the adhesive action of the mucoadhesive formulation commences. Even if the treated animal tries to remove the medicament form by chewing or sucking, this only gives additional support to the adhesion of the system.

In this manner it is made possible to achieve a simple and safe application of active substance, and more particularly it is ensured that the intended active substance dose is taken up since due to the adhesion to the mucosa it is no longer possible that the administration form is spit out or expelled.

As the target mucosa are considered first of all the oral mucosa as well as the mucosae of the pharynx and the nose. This does not exclude that the medicinal preparations according to the invention may also be applied to other mucosae of the human or animal body such as, for example, intestinal or vaginal mucosae.

In principle the mucoadhesive medicinal preparations according to the invention are suitable for the release of active substances in all body cavities which are lined by a mucosa, thus also for application in the uterus, for example.

After the medicinal form has been applied to a surface of a mucosa and adheres to the same, it starts to disintegrate under the action of moisture or of the surrounding aqueous medium, e.g. body fluids. Simultaneously the active substance contained in the medicament form is released and can now be absorbed via the mucosa concerned, e.g. the oral mucosa, or be transported further by the surrounding body fluids (e.g. saliva) and absorbed elsewhere. For example, the active substances released by the active substance preparation adhering to the oral mucosa can be dissolved or dispersed in the saliva. Subsequently, this saliva-active substance solution enters the gastro-intestinal tract where the active substance(s) are absorbed. Preferably, the preparations according to the invention are oral administration forms.

The disintegration process has substantially come to an end within 15 minutes provided that the administration form adhering to the mucosa was surrounded during this time by an aqueous medium, e.g. a body fluid. According to preferred embodiments of the invention, the medicament forms are adapted so as to disintegrate within 3 minutes, and with particular preference within 60 s, after having been introduced in an aqueous medium.

The disintegration times indicated are based on the disintegration time measurements according to Pharm. Eur. 2.9.1 "Zerfallszeiten von Tabletten und Kapseln" [Disintegration Times of Tablets and Capsules].

The indicated disintegration times can be adjusted within the ranges mentioned by using matrix-forming polymers which have different disintegration or solubility characteristics. For example, a wafer based on polyvinyl alcohol disintegrates much more rapidly than an HPMC wafer. By mixing appropriate polymer components it is thus possible to adjust the disintegration time. In addition, disintegrants are known which "draw" water into the matrix and explode the matrix from within. Consequently such disintegrants may also be added for the purpose of adjusting the disintegration time.

The rapidly disintegrating mucoadhesive medicinal preparations according to the invention are preferably flat-shaped bodies, designated as "wafers" in the following. Furthermore, it is also possible to produce these preparations in the form of pellets, capsules or tablets.

The above-mentioned wafers are comparatively dense bodies and preferably have a densitiy between 0.3 g/cm$^3$ and 1.7 g/cm$^3$, with particular preference between 0.5 g/cm$^3$ and 1.5 g/cm$^3$, and with greatest preference between 0.7 g/cm$^3$ and 1.3 g/cm$^3$.

The overall thickness of the inventive preparations, especially of the wafers, preferably amounts to 5 µm to 10 mm, preferably 30 µm to 2 mm, and with particular preference 0.1 mm to 1 mm. The wafers may advantageously be of round, oval, elliptic, triangular, quadrangular or polygonal shape, but may also be of any rounded shape.

The surface of the preparations according to the invention is usually smooth; it may, however, be of advantage to provide the surface with elevations and deepenings, e.g. in the form of knobs or grooves.

The invention also includes preparations of the kind mentioned which are present in the form of thin, solid foams. Wafers in the form of thin foams are advantageous since they quickly adhere to the mucosa due to their large specific surface, and since they on the other hand also disintegrate quickly. The density of these solidified foams is preferably between 0.01 g/cm$^3$ and 0.8 g/cm$^3$, with particular preference between 0.08 g/cm$^3$ and 0.4 g/cm$^3$, and with greatest preference between 0.1 g/cm$^3$ and 0.3 g/cm$^3$. When calculating the density, the volume filled or enclosed by the entire foam body is taken as the basis for calculation. The above-mentioned foams may be produced by introducing and dispersing gases with the aid of special foam beating devices, or by dissolving gas under pressure and subsequent relaxation of the solution.

The mucoadhesive, disintegratable matrix of the inventive medicinal preparations has at least one matrix-forming polymer. The matrix-forming polymer(s) constitute(s) a substantial component of the matrix. The polymer portion amounts to at least 3%-wt. and maximally 98%-wt., preferably 7 to 80%-wt., with particular preference 20 to 50%-wt., each value being relative to the entire preparation. The mucoadhesive properties as well as the disintegration properties are determined substantially by the type of the matrix-forming polymer(s), as well as by the relative portions of these polymers in the preparation.

As matrix-forming polymers which can be components of a mucoadhesive formulation according to the present invention, the following polymers are taken into consideration—without wishing to exclude other suitable raw materials:

Polyvinyl alcohol (e.g. Mowiol®); cellulose derivatives such as hydroxypropylmethyl cellulose, hydroxypropyl cellulose, sodium-carboxymethyl cellulose (e.g. Walocel), methyl cellulose, hydroxethyl cellulose and hydroxypropylethyl cellulose; starch and starch derivatives; gelatine (various types); polyvinyl pyrrolidone; gum Arabic; pullulan; acrylates; polyethylene oxide, especially the types of Polyox 10, Polyox 80, Polyox 205, Polyox 301, Polyox 750 (by the firm of Union Carbide); copolymers of methylvinyl ether and maleic acid anhydride (Gantrez-Copolymers, especially the types of ES, MS, S; by the firm of ISP Global Technologies GmbH).

Apart from the matrix-forming polymers, auxiliaries may optionally be added to the matrix. For this purpose the following are taken into consideration: fillers (e.g. $SiO_2$); dyes and pigments (e.g. chinoline yellow or $TiO_2$); disintegrants, especially disintegrants which draw water into the matrix and which burst the matrix from within (e.g aerosil); emulsifiers (e.g. polyethoxylated sorbitane fatty acid esters such as TWEEN® or polyethoxylated fatty alcohols such as BRIJ®); plasticizers (e.g. polyethylene glycol, glycerol); sweeteners (e.g. aspartame, saccharin); preserving agents (e.g. sorbic acid and its salts), and flavouring agents.

Furthermore, stabilisers or antioxidants may also be added as auxiliaries, such as, for example, ascorbyl palmitate, sodium disulfite, vitamin E, vitamin A, vitamin C; both singly and in combination with each other, or in combination with other auxiliaries.

According to a preferred embodiment the preparations according to the invention contain at least one flavouring substance and/or at least one sweetener and/or at least one plasticizer.

Addition of flavouring agents is advantageous because this improves acceptance of the medicinal preparation by the animal to be treated if the preparation is taken in by the direct, oral route. An unpleasant smell or taste caused by the medicinal active substance can be covered up by admixing a suitable flavouring agent. Preferably, when selecting such substances, the known preferences of the animals to be treated are taken into consideration. It is known, for example, that cheese, cream and valerian flavours can be advantageously utilized in medicinal preparations which are intended for administration to cats. Moreover, meat, sausage and fish flavours can be used with advantage to increase an animal's willingness to take a medicament preparation by the oral route. For certain groups of animals, however, fruit or herb flavours such as banana, strawberry, mint, cocoa, nut or coffee flavours are advantageous; likewise mixtures of different flavours can be used.

Likewise, when selecting the above-mentioned dyes or pigments, one should consider the faculties of perception of the treated animals. Thus, for example, a dark colour of the system (that is, of the medicinal preparation) e.g. in the colours blue or black, is especially advantageous for cats, in particular, as cats are only capable of distinguishing between black and white.

The mucoadhesive matrix in addition contains one or more pharmaceutical active substances; these are preferably active substances which are used in veterinary medicine for therapeutic purposes. Moreover, the active substances may be such as are used in drug therapy in human medicine. The active substance content amounts to at least 0.1%-wt., but maximally 50%-wt., relative to the entire preparation.

In the following, active substances used in the veterinary medicinal field are mentioned which may be contained in the preparation according to the invention and which may be administered by means of said preparation; the list is not complete.

The pharmaceutical active substances used in veterinary medicine can be divided into groups according to ATCvet (Anatomical Therapeutic Chemical classification system for veterinary medicinal products); this is a widely used classification system. By means of the ATCvet Code, medicaments for animals can be divided into therapeutic categories. This greatly facilitates finding drugs for animals for certain indications and modes of application. The list comprises the following groups and individual substances:

QA—gastroenterologics and betaine, pepsine, citric acid, calcium carbonate, magnesium subcarbonate, sodium chloride, sodium phosphate, prifinium bromide, bismuth subcarbonate, Enterococcus (streptococcus) faecium, yeast, methionine, magnesium peroxide, pectin, tannin, neomycin, biotin, bismuth subnitrate, papaverin, sulfaguanidine, calcium phosphate, cholecalciferol, iron gluconate, nicotinamide, pyridoxine hydrochloride, retinol, riboflavine, thiamine, metronidazole, spiramycin;

QB—blood, and haematogenic organs;

QC—cardiovascular system; enalapril, furosemide, etilefrine, propentofyllin, benazepril, ramipril, nicergoline, pimobendan;

QD—dermatologics; alpha-tocopherol, chlorophenaminemaleine, cholecalciferol, inositol, lecithin, linolenic acid, mepyramine, prednisolone, retinol, biotin, griseofulvin, cefalexin,;

QG—gynaecologics, including sex hormones; chlorophyll, metamizol, nitrofurantoine, pyridoxine hydrochloride, ephedrine, chlormadinone, metergolin, tetrazyklin, estriol, megestrol, medroxyprogesterone;

QH—hormonal system (not including sex hormones); methionine, nicotinamide, pyridoxine hydrochloride, flumetason, prednisolone, hydroxyzine;

QJ—anti-infectives; ampicillin, amoxicillin, clavulanic acid, cefadroxil, cefalexin, clindamycin, difloxacin, doxycycline, enrofloxacin, lincomycin, marbofloxacin, sulfadimidin, sulfadimethoxin, trimethoprim, metronidazol, spiramycin;

QM—muscle and sceletal system; phenylbutazone, meloxicam, cyanocobalamin, dexamethason, carprofen, flunixin, phenylbutazone, pyridoxine hydrochloride, prednisolone, suxibuzone, aluminium magnesium silicate, niflumic acid, thiamine;

QN—nervous system; acepromazin, clomipramin, physostigmine, ketamine, selegiline, acetylsalicylic acid, paracetamol, phenylbutazon, detomedines); anaesthetics or sedatives such as, for example, medetomidines, detomidines, dexmedetomidines; antisedativa such as, for example, antipamezols; analgesics;

QP—parasiticides; epsiprantel, nitroscanat, piperazin, pyrantel, oxantel, fenbendazol, praziquantel, nitenpyram, praziquantel, febantel, flubendazol, milbemycinoxim, mebendazol, lufenuron, carnidazol, niclosamide, tetramisol;

QR—respiratory system; chlorophenaminemalein, dextromethorphan, ephedrine, guaifenesin, theophyllin;

QS—sense organs; betamethason, neomycin, dexamethason, gentamycin;

QV—various; mitotan.

Furthermore, pharmacologically active substances are taken into consideration which are contained in the classes or groups mentioned below:

α-adrenergic agonists; β-adrenergic agonists; α-adrenergic blockers; β-adrenergic blockers; alcohol withdrawal agents; aldose-reductase inhibitors; anabolics; narcotic analgesics, preferably codeine, morphine derivatives; non-narcotic analgesics, preferably salicylates and their derivatives; androgens; anaesthetics; appetite depressants; anthelmintics (active against cestodes, nematodes, Onchocerca, Schistosomae or trematodes); anti-acne agents; anti-allergics, anti-amoebic agents (amoebecidal agents); anti-androgens; agents against angina pectoris; antiarrhythmics; anti-arteriosclerotic agents; anti-arthritic/antirheumatic agents; antibacterial agents (antibiotics), preferably aminoglycosides, amphenicols, ansamycines, β-lactams (especially carbapenemes, cephalosporines, cephamycines, monobactams, oxacephemes, penicillins), lincosamides, macrolides, polypeptides, tetracyclines; synthetic antibacterial agents, preferably 2,4-diaminopyrimidines, nitrofuranes, chinolones and chinolone analogues, sulfonamides, sulfones; anticholinergics; anticonvulsants; antidepressants, preferably bicyclic antidepressants, hydrazides, hydrazines, pyrrolidones, tetracyclic antidepressants; tricyclic antidepressants, polycyclic imides; antidiabetic agents, preferably biguanides, sulfonyl-urea derivatives; antidiarrhoeal agents; antidiuretics; anti-estrogens; antimycotics/fungicidal agents, preferably polyenes; synthetic antimycotics/fungicidal agents, preferably allylamines, imidazoles, triazoles; antiglaucoma agents; antigonadotropins; agents against gout; antihistaminics, preferably alkylamine derivates, aminoalkyl ethers, ethylenediamine derivates, piperazines, tricyclic compounds (especially phenothiazines); antihyperlipoproteinaemic agents (lipid-lowering agents), preferably aryloxyalcanoic acid derivates (especially clofibrinic acid derivatives and analogues), bile acid-sequestering (masking) substances, HMG-COA-reductase inhibitors, nicotinic acid derivatives, thyroid gland hormones and analogues thereof; anti-hypertensive/blood pressure-lowering agents, preferably benzothiadiazine derivatives, N-carboxyalkyl-(peptide/lactam) derivatives, guanidine derivatives, hydrazines/phthalazines, imidazol derivatives, quaternary ammonium compounds, chinazoline derivatives, reserpine derivatives, sulphonamide derivatives; agents against hyperthyroidism; agents against hypotension; agents against hypothyrosis; non-steroidal anti-inflammatory agents (antiphlogistics), preferably aminoarylcarboxylic acid derivatives, arylacetic acid derivatives, arylbutyric acid derivatives, arylcarboxylic acid derivatives, arylpropionic acid derivatives, pyrazoles, pyrazolones, salicylic acid derivatives, thiazinecarboxamide; antimalarial agents, preferably chinine and its salts, acids and derivatives; anti-migraine agents; agents against nausea; antineoplastic agents, preferably alkylating agents (especially alkyl sulfonates, aziridines, ethyleneimines and methylmelamines, nitrogen mustard gases, nitrosoureas), antibiotic agents, antimetabolites (especially folic acid analogues, purine analogues, pyrimidin analogues), enzymes, interferones, interleukines; hormonal antineoplastic agents, preferably androgens, anti-adrenal agents, anti-androgens, anti-estrogens (especially aromatase inhibitors); antineoplastic dietary additives; anti-Parkinson agents; agents against pheochromocytomae; agents against pneumocystis; agents for treating hypertrophy of the prostate; protozoacide agents, preferably against Leishmania, Trichomonas, Trypanosoma; antipruritic agents; antipsoriatic agents; antipsychotic agents, preferably butyrophenones, phenothiazines, thioxanthenes, other tricyclic agents, 4-arylpiperazine, 4-arylpiperidine; antipyretic agents; agents against rickettsiae; agents against seborrhoea; antiseptics, preferably guanidine, halogenes and halogen compounds, nitrofuranes, phenols, chinolines; antispasmodic/spasmolytic agents; antithrombotics; antitussives; anti-ulcus agents; uricostatics (antiurolithics); antivenenum; antiviral agents, preferably purines, pyrimidinones; anxiolytics, preferably arylpiperazines, benzodiazepine derivatives, carbamates; benzodiazepine antagonists; bronchodilators, preferably ephedrine derivatives, quaternary ammonium compounds, xanthine derivatives; calcium channel blockers, preferably arylalkylamines, dihydropyridine derivatives, piperazine derivatives; calcium regulators; cardiotonics; chelate or complex formers; cholecystokinine antagonists; cholelitholytic agents; choleretics; cholinergics; cholinesterase inhibitors; cholinesterase reactivators; CNS stimulants; decongestion agents; prophylactic agents against dental caries; depigmenting agents; diuretics, preferably organic mercury compounds, pteridines, purines, steroids, sulphonamide derivatives, uracils; dopamine receptor agonists; agents against ectoparasites; enzymes, preferably digestive enzymes, penicillin-inactivating enzymes, proteolytic enzymes; enzyme-inducing agents; steroidal and non-steroidal estrogens; gastric secretion inhibitors; glucocorticoids; gonad-stimulating active agents; gonadotropic hormones; growth hormone inhibitors; growth hormone-releasing factor; growth stimulants; haemolytic agents; heparin antagonists; hepato-protective agents, agents for treating diseases of the liver; immunomodulatores; immunosuppressing agents; ion exchange resins; lactation-stimulating hormones; LH-RH agonisten; lipotropic agents; agents against lupus erythematosus; mineralocorticoids; miotics; monoaminoxidase inhibitors; mucolytics; muscle relaxants; narcotics antagonists; neuroprotective agents; nootropics; ophthalmics; ovarian hormones; oxytozics; pepsin-inhibitors; peristaltic stimulants; progestogens; prolactin inhibitors; prostaglandins and prostaglandine analogues; protease inhibitors; respiratory stimulants; sclerosing agents; sedatives/hypnotics, preferably acyclic ureides, alcohols, amides, barbituric acid derivatives, benzodiazepine derivatives, bromides, carbamates, chloral derivatives, piperidinediones, chinazolone derivatives; thrombolytics; thyreotropic hormones; uricosurics; vasodilators (cerebral); vasodilators (coronary); vasodilators (peripheral); vasoprotective agents; vitamins, vitamin precursors, vitamin extracts, vitamin derivatives; vulneraries.

The above list is not complete. It includes both active substances that are used in human medicine therapy or prophylaxis, and active substances which can be used in veterinary medicine.

To support the active substance uptake, a further preferred embodiment provides for the addition of agents which accelerate the uptake of active agent (enhancers). Suitable enhancers are, in particular: propanediol, dexpanthenol, oleic acid; the enhancer(s) may, for example, be selected from the following group: saturated or unsaturated fatty acids, hydrocarbons, straight-chain or branched fatty alcohols, dimethyl sulfoxide, propylene glycol, decanol, dodecanol, 2-octyldodecanol, glycerol, isopropylidene glycerol, transcutol (=diethyleneglycol-monoethyl ether), DEET (=N,N-diethyl-m-tolueneamide), solketal, ethanol or other alcohols, menthol and other essential oils or components of essential oils, lauric acid diethanolamide, D-alpha-toco-pherol and dexpanthenol; the above list is not complete. Combinations of two or more enhancer substances can also be used to advantage.

The uptake of active substance can furthermore be improved by means of substances stimulating the blood flow which can be added to the preparations according to the invention.

Among these are, in particular: menthol, eucalyptol, ginkgo extract, geranium oil, camphor, spearmint oil, oil of juniper and rosmary. These blood flow-stimulating substances may be used singly or in combination with one or more of the afore-mentioned enhancers.

The inventive mucoadhesive preparations can advantageously be used for administering active substances to pets, domestic or useful animals or other animals, as well as to humans, especially for oral administration of medicaments. The application of active agents by means of the preparations according to the invention can be used with particular advantage in middle-sized domestic animals such as cats, dogs or rabbits, in small animals such as hamsters or mice as well as in big animals such as big cats (lion, tiger), or working animals and livestock (cattle, sheep, horse). The administration form can be applied directly into the animal's mouth but may also be administered with the aid of an applicator. Furthermore, the preparations according to the present invention can be mixed with the feedstuff, in which case dried feedstuff should be given preference (however, this does not exclude feedstuffs containing moisture).

The composition of the preparations according to the invention will be illustrated by way of example with reference to the following recipes:

EXAMPLE 1

| | |
|---|---|
| Walocel[(1)] CRT 30 | 61.2%-wt. |
| Metolose[(2)] 60SH-50 | 8.46%-wt. |
| Water[(4)] | |
| Chlorphenamine* | 10%-wt. |
| Propanediol | 5.4%-wt. |
| Mowiol[(3)] 15-79 | 12.24%-wt. |
| Flavour | 2.7%-wt. |

EXAMPLE 2

| | |
|---|---|
| Walocel[(1)] CRT 30 | 82.5%-wt. |
| Chlorphenamine* | 10%-wt. |
| Propanediol | 4.5%-wt. |
| Water[(4)] | |
| Aspartame | 3%-wt. |

EXAMPLE 3

| | |
|---|---|
| Water: alcohol[(4)] | |
| Active substance | 20%-wt. |
| Polyox 10 | 39.98%-wt. |
| Propanediol-1,2 | 10%-wt. |
| Dexpanthenol | 10%-wt. |
| Menthol | 10%-wt. |
| Eucalyptol | 10%-wt. |
| Azorubin | 0.02%-wt. |

EXAMPLE 4

| Water:(4) | |
|---|---|
| Active substance | 15%-wt. |
| Gantrez MS 955 | 25%-wt. |

*Active substance
(1)sodium-carboxymethyl cellulose
(2)tradename for hydroxymethylpropyl cellulose (HPMC)
(3)by the firm of Hoechst/Aventis AG
(4)the portion of water (or water-alcohol portion; Example 3) amounts to between 80 and 90% in manufacture, relative to the dry portion.

Wafer Production
According to the recipes of Examples 1 and 2:

EXAMPLE 1

The indicated portion of polyvinyl alcohol is dissolved in water at 90° C. Subsequently, the solution is again cooled down to room temperature and propanediol is added. Subsequently, the active substance is added. Then Walocel CRT 30 and metolose 60SH-50 are added in portions while stirring. Finally, the flavour (e.g. cream flavour) is incorporated. The solution is finished when all the components have been dissolved. The solution is cast onto a film and dried; subsequently the film is separated by longitudinal and crosswise cutting, so that individual wafers are obtained.

EXAMPLE 2

Walocel CRT 30 is dissolved in cold water, subsequently propanediol and aspartame are added. Finally, the active substance is added. The solution is finished when all the components have been dissolved. The solution is cast onto a film and dried; finally the film is separated by cutting lengthwise and crosswise, so that individual wafers are obtained.

The invention claimed is:

1. A mucoadhesive medicinal preparation for administering active substances in veterinary medicine, containing at least one active substance, wherein the preparation is a mucoadhesive matrix disintegratable in aqueous media, which matrix contains a mixture of matrix-forming polymers which mixture comprises sodium carboxymethyl cellulose, polyvinyl alcohol and hydroxypropylmethyl cellulose, said matrix being prepared from a solution containing said mixture of polymers, wherein the proportion of said polymers amounts to at least 3%-wt. and maximally 98%-wt. relative to the total preparation, and at least one active substance is dissolved or dispersed in said matrix, and wherein said preparation disintegrates or erodes within maximally 15 minutes after introduction in an aqueous medium or in body fluids, and said medicinal preparation is a wafer having a density between 0.3 g/cm$^3$ and 1.7 g/cm$^3$.

2. A mucoadhesive medicinal preparation for administering active substances in veterinary medicine, containing at least one active substance, wherein the preparation is a mucoadhesive matrix disintegratable in aqueous media, which matrix contains a mixture of matrix-forming polymers which mixture comprises sodium carboxymethyl cellulose, polyvinyl alcohol and hydroxypropylmethyl cellulose, said matrix being prepared from a solution containing said mixture of polymers, wherein the proportion of said polymers amounts to at least 3%-wt. and maximally 98%-wt. relative to the total preparation, and at least one active substance is dissolved or dispersed in said matrix, and wherein said preparation disintegrates or erodes within maximally 15 minutes after introduction in an aqueous medium or in body fluids, wherein the preparation is in the form of a wafer and the total thickness of the wafer is 5 μm to 10 mm, said wafer having a density between 0.3 g/cm$^3$ and 1.7 g/cm$^3$.

3. The mucoadhesive medicinal preparation according to claim 1, that disintegrates within 3 minutes after its introduction in an aqueous medium.

4. The mucoadhesive medicinal preparation according to claim 1, comprising at least one auxiliary substance, which auxiliary substance(s) is/are selected from the group consisting of fillers, colourants, disintegrants, emulsifiers, plasticizers, sweeteners, preservatives, stabilisers, antioxidants and flavours.

5. The mucoadhesive medicinal preparation according to claim 4, comprising at least one of a flavour, a sweetener and a plasticizer.

6. The mucoadhesive medicinal preparation according to claim 1, comprising at least one enhancer and/or at least one substance stimulating blood flow.

7. The mucoadhesive medicinal preparation according to claim 1, wherein the medicinal preparation that has a shape that is elliptical, oval, triangular, quadrangular, polygonal, or irregularly rounded.

8. The mucoadhesive medicinal preparation according to claim 1, wherein the density of said wafer is between 0.5 g/cm$^3$ and 1.5 g/cm$^3$.

9. The mucoadhesive medicinal preparation according to claim 1, wherein the mixture of matrix-forming polymers further comprises at least one selected from the group consisting of hydroxyropyl cellulose, methyl cellulose, hydroxyethyl cellulose, hydroxypropylethyl cellulose, starch and starch derivatives, gelatine, polyvinyl pyrrolidone, gum arabic, pullulan, acrylates, polyethylene oxide and copolymers of methylvinyl ether and maleic acid anhydride.

10. The mucoadhesive medicinal preparation according to claim 1, comprising at least one active substance used in drug, therapy in veterinary or human medicine, and wherein said active substance is selected from the group consisting of gastroenterologic agents, cardiovascular agents, dermatologic agents, gynaecologic agents, sex hormones, hormones, agents having an influence on the hormonal system, anti-infectives, substances acting on the muscular and skeletal systems, substances acting, on the nervous system, analgesics, anaesthetics, sedatives, antisedatives, parasiticides, substances acting on the respiratory system, and substances acting on the sense organs.

11. A process for administering pharmaceutically active substance(s) to an animal body comprising applying an active substance-containing, mucoadhesive medicinal preparation as defined in claim 1 to a mucous membrane surface of said animal.

12. The mucoadhesive medicinal preparation according to claim 1, wherein the preparation contains at least one substance stimulating the blood flow.

13. The mucoadhesive medicinal preparation according to claim 1, wherein the preparation contains at least one substance accelerating the uptake of the active substance, said active substance being selected from the group consisting of propane diole, dexpanthenol, saturated fatty acids, unsaturated fatty acids, hydrocarbons, straight-chain fatty alcohols, branched fatty alcohols, dimethyl sulfoxide, 2-octyldodecanol, isopropylidene glycerol, diethyleneglycol-mono-ethyl ether, N,N-diethyl-m-tolueneamide, solketal, laurie acid diethanolamide and D-alpha-tocopherol.

14. The mucoadhesive medicinal preparation accordng to claim 2, wherein the total thickness of the preparation is 30 μm to 2 mm.

15. The mucoadhesive medicinal preparation according to claim 4, wherein the total thickness of the preparation is 0.1 mm to 2 mm.

16. The mucoadhesive medicinal preparation according to claim 1, wherein the preparation disintegrates within 60 seconds after its introduction in an aqueous medium.

17. The mucoadhesive medicinal preparation according to claim 1, wherein the mixture of matrix forming polymers consists of sodium carboxy methyl cellulose, polyvinyl alcohol and hydroxypropylmethyl cellulose.

18. The mucoadhesive medicinal preparation according to claim 1, wherein said preparation is obtained by casting and drying said solution.

19. The mucoadhesive medicinal preparation according to claim 1, wherein said matrix-forming polymers further include methyl cellulose, and the hydroxypropylmethyl cellulose and methyl cellulose are present in an amount of 8.46%-wt. relative to the total preparation.

20. The mucoadhesive medicinal preparation according to claim 1, wherein said proportion of said polymers amounts to 50%-wt. and maximally 98%-wt, relative to the total preparation and the matrix further optionally comprises stabilizer consisting of ascorbyl palmitate, sodium disulfite, vitamin E, vitamin A, vitamin C, or a combination thereof.

* * * * *

UNITED STATES PATENT AND TRADEMARK OFFICE
CERTIFICATE OF CORRECTION

PATENT NO.          : 8,906,406 B2                                  Page 1 of 1
APPLICATION NO.     : 10/468230
DATED               : December 9, 2014
INVENTOR(S)         : Rademacher et al.

It is certified that error appears in the above-identified patent and that said Letters Patent is hereby corrected as shown below:

In the Claims

Column 10
Claim 10, Line 36, delete "," after drug
Claim 10, Line 43, delete "," after acting Column 11
Claim 15, Line 2, delete "4" insert --2--

Signed and Sealed this
Seventh Day of April, 2015

Michelle K. Lee
*Director of the United States Patent and Trademark Office*